United States Patent
Altman et al.

(10) Patent No.: US 9,259,520 B2
(45) Date of Patent: Feb. 16, 2016

(54) BIPHASIC AND DYNAMIC ADJUSTABLE SUPPORT DEVICES AND METHODS WITH ASSIST AND RECOIL CAPABILITIES FOR TREATMENT OF CARDIAC PATHOLOGIES

(71) Applicants: The Texas A&M University System, College Station, TX (US); Corlnnova Incorporated, Houston, TX (US)

(72) Inventors: William C. Altman, Houston, TX (US); Saurabh Biswas, College Station, TX (US); John C. Criscione, College Station, TX (US); Lewis D. Harrison, Flower Mound, TX (US); Michael R. Moreno, Bryan, TX (US); Dennis I. Robbins, Richardson, TX (US)

(73) Assignees: THE TEXAS A&M UNIVERSITY SYSTEM, College Station, TX (US); CORINNOVA INCORPORATED, Houston, TX (US)

( * ) Notice: Subject to any disclaimer, the term of this patent is extended or adjusted under 35 U.S.C. 154(b) by 0 days.

(21) Appl. No.: 14/577,218

(22) Filed: Dec. 19, 2014

(65) Prior Publication Data
US 2015/0196697 A1 Jul. 16, 2015

Related U.S. Application Data

(62) Division of application No. 12/842,021, filed on Jul. 22, 2010, now Pat. No. 8,944,986.

(60) Provisional application No. 61/276,215, filed on Sep. 9, 2009, provisional application No. 61/271,559, filed on Jul. 22, 2009.

(51) Int. Cl.
*A61M 1/10* (2006.01)
*A61F 2/24* (2006.01)
*A61M 1/12* (2006.01)

(52) U.S. Cl.
CPC ............ *A61M 1/1068* (2013.01); *A61F 2/2481* (2013.01); *A61M 1/106* (2013.01); *A61M 1/122* (2014.02); *A61F 2220/0008* (2013.01); *A61F 2250/0003* (2013.01)

(58) Field of Classification Search
CPC . A61M 1/101; A61M 1/1065; A61M 1/1063; A61M 1/106; A61M 1/1037
USPC .................................................. 600/16, 17, 37
See application file for complete search history.

(56) References Cited

U.S. PATENT DOCUMENTS 2,826,193 A 3/1958 Vineberg
3,034,501 A 5/1962 Hewson (Continued)

FOREIGN PATENT DOCUMENTS

WO 9922784 A1 5/1999
WO 0036995 A2 6/2000

(Continued)

OTHER PUBLICATIONS

Anstadt, et al., "Non-blood contacting biventricular support for severe heart failure." Ann Thorac Surg (2002), 73:556-62.

(Continued)

*Primary Examiner* — Catherine Voorhees
*Assistant Examiner* — Roland Dinga
(74) *Attorney, Agent, or Firm* — Chainey P. Singleton; Edwin S. Flores; Chalker Flores, LLP

(57) ABSTRACT

The present invention provides a biphasic and dynamic direct cardiac contact device adapted to be implanted in a patient suffering from congestive heart failure and related cardiac pathologies, said cardiac device having means for providing ventricular assist, ventricular support and diastolic recoil, or for providing ventricular support and diastolic recoil only.

7 Claims, 6 Drawing Sheets

(56) References Cited

U.S. PATENT DOCUMENTS

| | | | |
|---|---|---|---|
| 3,233,607 A | 2/1966 | Bolie | |
| 3,513,836 A | 5/1970 | Sausse | |
| 4,048,990 A | 9/1977 | Goetz | |
| 4,185,617 A | 1/1980 | Hutchins | |
| 4,536,893 A | 8/1985 | Parravicini | |
| 4,685,446 A | 8/1987 | Choy | |
| 5,089,017 A | 2/1992 | Young et al. | |
| 5,119,804 A | 6/1992 | Anstadt | |
| 5,131,905 A | 7/1992 | Grooters | |
| 5,169,381 A | 12/1992 | Snyders | |
| 5,256,132 A | 10/1993 | Snyders | |
| 5,348,528 A | 9/1994 | Vince | |
| 5,483,958 A | 1/1996 | Merberg et al. | |
| 5,562,730 A | 10/1996 | Davidson | |
| 5,738,627 A | 4/1998 | Kovacs et al. | |
| 5,749,839 A | 5/1998 | Kovacs | |
| 5,863,574 A | 1/1999 | Julien | |
| 6,155,968 A | 12/2000 | Wilk | |
| 6,224,540 B1 | 5/2001 | Lederman et al. | |
| 6,293,906 B1 | 9/2001 | Vanden Hoek et al. | |
| 6,387,042 B1 | 5/2002 | Herrero | |
| 6,540,666 B1 | 4/2003 | Chekanov | |
| 6,592,619 B2 | 7/2003 | Melvin | |
| 6,595,912 B2 | 7/2003 | Lau et al. | |
| 6,602,182 B1 | 8/2003 | Milbocker | |
| 6,602,184 B2 | 8/2003 | Lau et al. | |
| 6,612,978 B2 | 9/2003 | Lau et al. | |
| 6,612,979 B2 | 9/2003 | Lau et al. | |
| 6,626,821 B1 | 9/2003 | Kung et al. | |
| 6,663,558 B2 | 12/2003 | Lau et al. | |
| 6,723,039 B2 | 4/2004 | French et al. | |
| 6,784,283 B2 | 8/2004 | Andersen et al. | |
| 7,097,611 B2 | 8/2006 | Lau et al. | |
| 7,229,405 B2 | 6/2007 | Lau et al. | |
| 7,275,542 B2 | 10/2007 | Lurie et al. | |
| 7,445,593 B2 | 11/2008 | Criscione | |
| 7,489,380 B2 | 2/2009 | Lim et al. | |
| 7,494,459 B2 | 2/2009 | Anstadt et al. | |
| 7,674,222 B2 | 3/2010 | Nikolic et al. | |
| 7,871,366 B2 | 1/2011 | Criscione et al. | |
| 7,935,045 B2 | 5/2011 | Criscione et al. | |
| 8,011,367 B2 | 9/2011 | Lurie et al. | |
| 8,075,471 B2 | 12/2011 | Trumble | |
| 8,187,160 B2 | 5/2012 | Criscione et al. | |
| 8,192,351 B2 | 6/2012 | Fishler et al. | |
| 8,550,976 B2 | 10/2013 | Criscione | |
| 8,944,986 B2 | 2/2015 | Altman et al. | |
| 2002/0007216 A1 | 1/2002 | Melvin | |
| 2002/0065449 A1 | 5/2002 | Wardle | |
| 2003/0088151 A1 | 5/2003 | Kung et al. | |
| 2004/0010180 A1 | 1/2004 | Scorvo | |
| 2005/0004420 A1 | 1/2005 | Criscione | |
| 2005/0187425 A1 | 8/2005 | Alferness et al. | |
| 2005/0217677 A1 | 10/2005 | Lurie et al. | |
| 2006/0241334 A1 | 10/2006 | Dubi et al. | |
| 2006/0276683 A1 | 12/2006 | Feld et al. | |
| 2006/0287568 A1 | 12/2006 | Jassawalla et al. | |
| 2007/0015958 A1 | 1/2007 | Lau et al. | |
| 2007/0016184 A1 | 1/2007 | Cropper et al. | |
| 2007/0161846 A1 | 7/2007 | Nikolic et al. | |
| 2007/0208214 A1 | 9/2007 | Hjelle et al. | |
| 2007/0221222 A1 | 9/2007 | Lurie et al. | |
| 2007/0276444 A1 | 11/2007 | Gelbart et al. | |
| 2008/0021260 A1* | 1/2008 | Criscione et al. ............ 600/16 |
| 2008/0071134 A1 | 3/2008 | Dubi et al. | |
| 2008/0257344 A1 | 10/2008 | Lurie et al. | |
| 2009/0036730 A1 | 2/2009 | Criscione et al. | |
| 2009/0062701 A1 | 3/2009 | Yannopoulos et al. | |
| 2009/0318746 A1 | 12/2009 | Thurmond, II et al. | |
| 2010/0081867 A1 | 4/2010 | Fishler et al. | |
| 2010/0152531 A1 | 6/2010 | Goodman et al. | |
| 2010/0249519 A1 | 9/2010 | Park et al. | |
| 2011/0034776 A1 | 2/2011 | Dixon et al. | |
| 2011/0040152 A1 | 2/2011 | Kim et al. | |
| 2011/0166410 A1 | 7/2011 | Gutierrez et al. | |
| 2013/0102849 A1 | 4/2013 | Criscione et al. | |
| 2013/0150923 A1 | 6/2013 | Schnetz et al. | |

FOREIGN PATENT DOCUMENTS

| | | |
|---|---|---|
| WO | 03001971 A2 | 1/2003 |
| WO | 2004112867 A1 | 12/2004 |
| WO | 2006108177 A2 | 10/2006 |
| WO | 2007062239 A2 | 5/2007 |
| WO | 2008154033 A2 | 12/2008 |
| WO | 2009018358 A2 | 2/2009 |
| WO | 2011011641 A2 | 1/2011 |
| WO | 2011011642 A2 | 1/2011 |
| WO | 2012075460 A2 | 6/2012 |
| WO | 2012094064 A1 | 7/2012 |
| WO | 2013059316 A2 | 4/2013 |

OTHER PUBLICATIONS

Artrip, et al., "Physiological and hemodynamic evaluation of non-uniform direct cardiac compression." Circulation (1999), 100 (suppl ll):236-43.

Cohn, et al. "Cardiac Remodeling -Concepts and Clinical Implications: A Consensus Paper From an International Forum on Cardiac Remodeling" Journal of the American College of Cardiology vol. 35, No. 3, Mar. 1, 2000.

Cooley, et al. "The past 50 years of cardiovascular surgery" (2000) Circulation 102: IV88-93.

Dipla, et al., "Myocyte recovery after mechanical circulatory support in humans with end-stage heart failure." Circulation (1998), 97:2316-2322.

Feldman, et al. "Selective changes in cardiac gene expression during compensated hypertrophy and the transition to cardiac decompensation in rats with chronic aortic banding" (1993). Circ. Res. 73: 184-192.

Ghanta, et al, "Adjustable, Physiological Ventricular Restraint Improves Left Ventricular Mechanics and Reduces Dilation in an Ovine Model of Chronic Heart Failure," Mar. 13, 2007, Circuilation (10):12-1-10.

Ghanta, et al, "Real-time Adjustment of Ventricular Restraint Therapy in Heart Failure," Dec. 2008, Eur. J. Cardiothorac Surg., 34(6):1136-40, available online Aug. 19, 2008.

Gheorhiad, et al. "Chronic heart failure in the united states: a manifestation of coronary artery disease" (1998) Circulation 97:282-9.

Goldstein, et al., "Medical progress: implantable left ventricular assist devices." N. Engl J Med (Nov. 19, 1998), 339 (21):1522-1533.

Heerdt, et al., "Chronic unloading by left ventricular assist device reverses contractile dysfunction and alters gene expression in end-stage heart failure." Circulation (2000), 102:2713-2719.

Karvarana, et al., "Circulatory support with a direct cardiac compression device: a less invasive approach with the AbioBooster device." J Thorac Cardiovasc Surg (Oct. 2001), 122:786-787.

Kawaguchi, et al., "Mechanical enhancement of myocardial oxygen saving by synchronized dynamic left ventricular compression." J Thorac Cardiovasc Surg (1992), 103:573-81 (Abstract Only).

Kherani, et al., "Ventricular assist devices as a bridge to transplant or recovery." Cardiol (2004), 101:93-103.

Mann, et al, "Left Ventricular Size and Shape: Determinants of Mechanical Signal Transduction Pathways," 2005, Heart Failure Reviews, vol. 10, No. 2, pp. 95-100.

Mann, et al, "Mechanisms and Models in Heart Failure: the Biomechanical Model and Beyond," May 31, 2005, Circulation, 111(21):2837-49.

Moreno, et al, "Assessment of Minimally Invasive Device That Provides Simultaneous Adjustable Cardiac Support and Active Synchronous Assist in an Acute Heart Failure Model," Journal of Medical Devices, Dec. 2011, vol. 5 / 041008-1.

Omens, J.H. "Stress and strain as regulators of myocardial growth." Prog. Biophys. Molec. Biol. (1998), 69:559-572.

Oz, et al., "Direct cardiac compression devices." J Heart Lung Transplant (2002), 21:1049-1055.

(56) References Cited

OTHER PUBLICATIONS

Rose, et al., "Long-term use of left ventricular assist device for end-stage heart failure." N Engl J Med (Nov. 15, 2001), 345(20):1435-1443.

Tamminen, et al., "Ectopic Expression of AB13 Gene Enhances Freezing Tolerance in Response to Abscisic Acid and Low Temperature in Arabidopsis Thaliana," The Plant Journal, (2001), 25(1):1-8.

Williams, et al. "Direct cardiac compression for cardiogenic shock with the CardioSupport System." Ann Thorac Surg (2001), 71:S188-9.

United States Patent & Trademark Office (ISA), International Search Report and Written Opinion for PCT/US2005/003343 dated Jul. 16, 2007.

European Patent Office, Supplementary European Search Report for EP 10802924.0 (PCT/US2010/042970), dated Sep. 27, 2012.

European Patent Office (ISA), Written Opinion for PCT/US2004/019809 dated Oct. 24, 2005—8 pp.

Korean Intellectual Property Office (ISA), International Search Report for PCT/US2010/042970, dated May 2, 2011, 13 pp.

Korean Intellectual Property Office (ISA), International Search Report and Written Opinion for PCT/US2010/042972, dated Apr. 14, 2011, 8 pp.

Korean Intellectual Property Office (ISA), International Search Report for PCT/US2008/071618 dated Feb. 12, 2009.

United States Patent & Trademark Office (ISA) (Corrected), International Search Report and Written Opinion for PCT/US2006/013457 dated Dec. 10, 2007.

Korean Intellectual Property Office (ISA), International Search Report and Written Opinion for PCT/US2011/063178 dated Jun. 25, 2012—14 pp.

Korean Intellectual Property Office (ISA), International Search Report and Written Opinion for PCT/US2012/060609 dated Apr. 19, 2013—15 pp.

\* cited by examiner

BIPHASIC AND DYNAMIC ADJUSTABLE SUPPORT DEVICES AND METHODS WITH ASSIST AND RECOIL CAPABILITIES FOR TREATMENT OF CARDIAC PATHOLOGIES

CROSS REFERENCE TO RELATED APPLICATION

This patent application is a divisional patent application of U.S. Ser. No. 12/842,021 filed on Jul. 22, 2010, which claims priority to U.S. Provisional Application Ser. No. 61/271,559, filed Jul. 22, 2009 and U.S. Provisional Application Ser. No. 61/276,215, filed Sep. 9, 2009, the contents of which are incorporated by reference herein in their entirety.

STATEMENT REGARDING FEDERALLY SPONSORED RESEARCH OR DEVELOPMENT

This invention was made with U.S. Government support under Contract No. IIP-0912711 awarded by the National Science Fund (NSF). The government has certain rights in this invention.

TECHNICAL FIELD OF THE INVENTION

The present invention relates to devices and methods designed to apply forces to the exterior surface of a heart to promote cardiac assist, support and diastolic recoil of a diseased or damaged heart with diastolic dysfunction, systolic dysfunction, or a combination of diastolic and systolic dysfunction.

BACKGROUND OF THE INVENTION

Congestive heart failure (CHF) is a major public health issue in the developed and developing world. In the U.S., CHF affects more than 5.7 million people with 550,000 new cases diagnosed each year. Approximately 20% of hospitalizations are due to acute CHF, incurring a health-care system cost of $37.2 billion (AHA statistics, 2009). Heart failure has two main forms: systolic dysfunction and diastolic dysfunction. Some people with heart failure have both types of dysfunction. In systolic dysfunction, the heart contracts less forcefully and cannot pump out as much of the blood that is returned to it as it normally does. As a result, more blood remains in the lower chambers of the heart (ventricles). In diastolic dysfunction, the heart is stiff and does not relax normally after contracting, which impairs its ability to fill with blood. The heart contracts normally, but is unable to pump a normal proportion of blood out of the ventricles because filling was sub-optimal. Often, both forms of heart failure (systolic and diastolic) occur together. Although systolic heart failure is more commonly mentioned, there is growing recognition that congestive heart failure (CHF) caused by a predominant abnormality in diastolic function (i.e., diastolic heart failure) is both common and causes significant morbidity and mortality. Diastolic heart failure can occur alone or in combination with systolic heart failure. In patients with isolated diastolic heart failure, the only abnormality in the pressure-volume relationship occurs during diastole, when there are increased diastolic pressures with normal diastolic volumes. When diastolic pressure is markedly elevated, patients are symptomatic at rest or with minimal exertion (NYHA class III to IV). With treatment, diastolic volume and pressure can be reduced, and the patient becomes less symptomatic (NYHA class II), but the diastolic pressure-volume relationship remains abnormal.

In patients with systolic heart failure, there are abnormalities in the pressure-volume relationship during systole, which includes decreased ejection fraction (EF), stroke volume, and stroke work. In addition, there are changes in the diastolic portion of the pressure-volume relationship. These changes result in increased diastolic pressures in symptomatic patients, which indicate the presence of combined systolic and diastolic heart failure. Whereas the diastolic pressure-volume relationship may reflect a more compliant chamber, increased diastolic pressure and abnormal relaxation reflect the presence of abnormal diastolic function. Thus, all patients with systolic heart failure and elevated diastolic pressures likely have combined systolic and diastolic heart failure.

Another form of combined systolic and diastolic heart failure is also possible. Patients may have only a modest decrease in EF and a modest increase in end-diastolic volume but a marked increase in end-diastolic pressure and a diastolic pressure-volume relationship that reflects decreased chamber compliance. Therefore, all patients with symptomatic heart failure potentially have abnormalities in diastolic function; those with a normal EF have isolated diastolic heart failure, and those with a decreased EF have combined systolic and diastolic heart failure.

Heart failure typically begins after an "index event" produces an initial decline in pumping capacity of the heart. Following this initial decline in pumping capacity of the heart, a variety of compensatory mechanisms are activated, including the adrenergic nervous system, the renin angiotensin system and the cytokine system. In the short term these systems are able to restore cardiovascular function to a normal homeostatic range with the result that the patient remains asymptomatic. However, with time the sustained activation of these systems can lead to secondary end-organ damage within the ventricle, with worsening left ventricle (LV) remodeling and subsequent cardiac decompensation. As a result of resultant worsening LV remodeling and cardiac decompensation, patients undergo the transition from asymptomatic to symptomatic heart failure (Heart Failure Reviews, 10, 95-100, 2005).

In systolic heart failure, the LV undergoes a transformation from a prolate ellipse to a more spherical shape resulting in an increase in meridional wall stress of the LV, which in turn creates a number of de novo mechanical burdens for the failing heart. This LV remodeling dramatically alters the mechanical environment, which in turn influences growth and remodeling processes. A positive feedback loop emerges leading to acute dysfunctional cardiac pumping, pathologic neurohormonal activation, and the inability of the remodeled LV to respond appropriately to compensatory mechanisms.

Progressive LV dilation and subsequent remodeling is one of the mechanisms that lead to LV wall stress and myocardial stretch. Increased LV wall stress may lead to sustained expression of stretch-activated genes (angiotensin II, endothelin and tumor necrosis factor) and/or stretch activation of hypertrophic signaling pathways as stretch triggers myocyte responses both by inducing the release of humoral factors that are important in the initiation and maintenance of hypertrophy, as well as via the direct activation of signaling pathways as well.

LV dilation and increased LV sphericity are also sensitive indicators of poor long-term outcome. Thus, cardiac wall stress (which can be defined as the "force per unit of cross-sectional area") of the ventricular wall is directly related to the difference in pressure between the ventricles and ventricular radius, and inversely related to ventricular wall thickness. So with LV remodeling, an increase in ventricular volumes and a subsequent increase in ventricular radius, a larger force is required from each individual myocyte to produce enough pressure in the ventricles. Wall tension is seen as a function of both internal pressure and vessel radius. Also, with ventricular remodeling, cardiac mass can increase, with a corresponding increase in ventricular wall thickness. Any such increase in wall thickness would result from remodeling at the cellular/extracellular matrix level by several processes including myocyte hypertrophy, cell slippage, and interstitial growth. However, such increases in wall thickness do not adequately compensate for the increase in wall stress resulting from cardiac chamber dilation with an increasing metabolic stress. Thus, ventricular remodeling is maladaptive, despite any incremental increase in ventricular wall thickness. Laplace's equation provides a framework for defining means of mitigating ventricular remodeling. Ventricular wall stress can be reduced by (1) decreasing transmural pressure; (2) reducing cardiac chamber radius; and/or (3) promoting greater ventricular wall thickness. A diastolic support device can have a significant impact on effective transmural pressure which can lead to a decrease in the diastolic wall stress and modulate the end-diastolic volume.

Of the 5.7 million people in the US and 25 million people worldwide who suffer from heart failure, between 30-55% of these patients suffer from diastolic heart failure (DHF) and are without effective treatment. The term diastolic heart failure (DHF) generally refers to the clinical syndrome of heart failure associated with a preserved left ventricular EF, in the absence of major valvular disease. Forty percent of incident CHF cases and 50-60% of prevalent CHF cases occur in the setting of preserved systolic function. Mortality rate among patients with DHF is considered lower than in systolic heart failure. Some challenge this notion, showing that the natural history of patients with DHF may not be different from that of patients with systolic heart failure. The morbidity and rate of hospitalization are similar to those of patients with systolic heart failure. Due to its higher prevalence in the elderly population, the incidence of DHF is expected to rise with the increased aging of the western world population. The fundamental problem in diastolic heart failure is the inability of the left ventricle to accommodate blood volume during diastole at normal filling pressures.

Two basic types of diastolic abnormalities may be present, impaired ventricular relaxation, which primarily affects early diastole, and increased myocardial stiffness, which primarily affects late diastole. The rate and extent of the active relaxation may influence LV suction during the early filling phase. Both abnormalities lead to elevation of diastolic pressures. In DHF patients, a relatively small increase in central blood volume or an increase in venous tone, arterial stiffness, or both, can cause a substantial increase in left atrial and pulmonary venous pressures and may result in exercise intolerance and acute pulmonary edema. The mechanisms underlying abnormalities in diastolic function can be divided into factors intrinsic to the myocardium itself and factors that are extrinsic to the myocardium. Myocardial factors can additionally be divided into cellular and extracellular. Cellular factors include impaired calcium homeostasis leading to abnormalities in both active relaxation and passive stiffness, changes in sarcomeric proteins isotypes, such as titin, which acts as a viscoelastic spring that gains potential energy during systole and provides a recoiling force to restore the myocardium to its resting length during diastole. Since relaxation is an energy consuming process, any abnormalities in cellular energy supply and utilization can lead to impaired relaxation. Extracellular factors include changes in structures and quantity of the extracellular matrix, i.e. fibrosis, that lead to increased myocardial stiffness. There is limited data on neurohumoral markers in DHF patients other than natriuretic peptides (NPs). This probably reflects the fact that DHF has only recently been recognized as an important clinical problem. The present work is towards development of a novel diastolic recoil device to manage patients with diastolic heart failure.

For treating systolic heart failure there are several classes of solutions, e.g., pharmaceuticals, stem cells, electrical devices, mechanical devices, and surgical reconstruction. Each of these are designed for some limited target action (i.e., beta-blockade, ACE inhibition, electrical pacing, cardiac assist, etc.); consequently, heart failure remains a cause of tremendous morbidity and healthcare burden. Conventional approaches fail to address the possibility that mechanical stimuli are important parameters for guiding growth and remodeling, processes that may ultimately facilitate the recovery of mechanical organs. The mechanical heart assist devices Class IIIA and IIIB are classified into active devices that provide pumping energy, and passive devices that modulate the shape of the heart. The active devices are subdivided into blood pumps, counter pulsation assist devices (aortic balloon pumps), and direct cardiac compression devices (DC-CDs). The passive, "support" devices directly interact with the heart to change shape or limit growth.

Diastolic heart failure therapies presently include mostly pharmaceutical products and there are few, if any, devices available. There are presently no approved devices for treatment of the DHF symptoms. However, two preclinical stage recoil device concepts, LEVRAM and Imcardia have a potential role in the treatment of DHF patients. These and other devices are seen in U.S. Patent Application Publication No. 2008/0071134, In Vivo Device for Assisting and Improving Diastolic Ventricular Function; U.S. Patent Publication No. 2006/0276683, In-Vivo Method and Device for Improving Diastolic Function of the Left Ventricle; and U.S. Patent Application Publication No. 2006/0241334, In Vivo Device for Improving Diastolic Ventricular Function.

Cardiac strain patterns appear to be a major controller of cardiac stem cell differentiation into functional cardiomyocytes. The exact normal or physiologic strain pattern of the heart is not currently known. Tests to determine the normal strain pattern in the heart of eight healthy sheep using bi-plane x-ray data of radio-opaque markers produced eight distinctly different patterns. It appears that cardiac contraction is similar to gait; there are gross similarities amongst individuals (e.g., toe off and hip twist), but the details can be distinctly different (e.g., angle of leg at toe off, amount and timing of the hip twist). In fact, people can often be recognized from their gait. While it is difficult to describe a normal gait, it is quite easy to classify abnormal gaits. Likewise, normal cardiac strain pattern is difficult to define and prescribe, yet it is quite easy to identify abnormal cardiac strain patterns such as dyskinesis and hypokinesis.

It is well established that mechanical stimuli (e.g., stress or strain) are important epigenetic factors in cardiovascular development, adaptation, and disease. In the vasculature, for example, it appears that perturbed loading conditions heighten the turnover of cells (proliferation and apoptosis) and matrix (synthesis and degradation) in altered configurations, thus resulting in altered geometries, properties, and biologic function. Just as similar mechanisms appear to be operative in hypertension, aneurysms, and micro-gravity induced changes, it is likely that they are operative in cardiac disease.

Dyskinesis or aberrant motion of the myocardium during contraction is likely important in all diseases of the heart that involve remodeling of the myocardium. Clearly, borderzone myocardium is viable yet overloaded to the extent that it is dyskinetic, i.e., lengthens when it should shorten. It is likely that overloading leads to aberrant remodeling because off-loading leads to: normalization of genes that regulate calcium handling, tumor necrosis factor and cytoskeleton proteins; regression of fibrosis and cellular hypertrophy, and improved in-vitro contractile function. Too much offloading is suspected to result in heart atrophy, whereby gradual weaning from a device should be sought along with combination therapy such as with clenbuterol.

At the cellular level, myofibrillar organization, sarcomere alignment and cell migration are all known to be mediated by mechanical factors. Mechanical factors are also known to play an important role in the behavior of stem cells, suggesting that understanding and control of the mechanical environment may be critical to the realization of the potential for stem cell therapies.

Cellular and subcellular investigations have established that altered hemodynamic loading leads to growth and remodeling of myocytes and extra-cellular matrix and myocytes are very sensitive to perturbations in strain and respond with altered gene expression. Abnormal cardiac kinematics is often considered as a symptom of heart failure when in actuality it may be a primary cause of the aberrant growth and remodeling. Other CHF mechanisms or co-contributors are, among others, loss of myocyte shortening capability, calcium dysregulation and unspecified myocyte apoptosis.

Regenerative therapies incorporating stem cells have demonstrated potential but have yet to be fully developed. Benefits observed in stem cell studies have been controversial, e.g., there is a general lack of evidence that implanted stem cells are actually integrating with the native tissue as functional cardiomyocytes. Stem cells are typically transplanted into the diseased myocardium where fiber alignment is highly disorganized and disrupted by fibrotic tissue. In the dyskinetic myocardium, the mechanical and environmental cues required to guide alignment and migration of transplanted cells are severely compromised. The device described herein, provides the means to restore motion that may be critical to establishing the appropriate physiologic mechanical environment required to optimize stem cell transplant therapies.

The various mechanical assist therapies (i.e., drugs, biventricular pacing, blood contacting assist devices, surgical manipulations, or passive stents and constraints etc.) typically off-load the heart and thus only modulate the strain pattern indirectly (e.g., through greater ejection fraction). Only direct cardiac compression devices (DCCDs) can directly induce a particular strain pattern. However, most prior DCCDs have been developed for enhancing ejection fraction or for ease of implantation rather than for strain modulation. Most induce aberrant strain patterns during contraction.

What follows is a discussion of the disadvantages of the prior art. FIGS. 1A-1D shows the normal, null, and inverted curvature in apex-to-base, radial plane (long axis) of the heart. FIG. 1A illustrates a normal or positive curve with the inside of the curve toward the chamber, where the top references the base and the bottom references the apex. FIG. 1B illustrates a null curvature. FIG. 1C illustrates an inverted or negative curvature where the inside of the curve is away from the chamber. FIG. 1D is an illustration that shows the curvature inversion of the Anstadt cup as illustrated in FIG. 9 of the Anstadt patent (U.S. Pat. No. 5,119,804). DCCDs have been characterized as most promising with good hemodynamics and ease of implantation. A number of DCCDs are being developed. The Anstadt cup is shown in FIG. 1D. The CardioSupport System by Cardio Technologies Inc. is similar to the Anstadt cup. The attachment is via vacuum on the apical end and the assist is via inflation of a membrane that lies between a rigid shell and the epicardial surfaces of the right ventricle (RV) and left ventricle (LV). The devices of Parravicini and the AbioBooster by Abiomed Inc. are sewn to the interventricular sulci, and elastic sacks between the shell and the epicardial surface are inflated during systole. The DCC Patch by Heart Assist Tech Pty Ltd. is similar to the AbioBooster. It has been described as " . . . two patches shaped to suit the profile of the heart . . . inflated and deflated in synchrony with the heart . . . " The heart booster is composed of longitudinal tubes that have elliptical cross-sections with the major axis of the ellipse in the hoop direction.

To understand how all of these DCCDs induce aberrant strain patterns, it is important to note that contraction strain depends on both the end-diastolic configuration (reference configuration) and the end-systolic configuration (current configuration). The strain field is a function of the gradient (with respect to reference position) of the mapping of material points from the reference configuration to the current configuration. Thus, the fact that prior DCCDs fit the diastolic configuration is inconsequential to achieving an appropriate contraction strain pattern because their end-systolic configurations are grossly aberrant. Although strains induced by such motions as torsion may not perturb the heart geometry; if the overall geometry is abnormal, then the strain must be abnormal. Unphysiological geometries are illustrated in FIGS. 1A-1D.

Generally, the curvature is inversely proportional to the radius-of-curvature and that curvature changes sign when the origin of the radius-of-curvature changes sides. As should be evident from FIG. 1D, curvature inversion can greatly increase EF. However, the curvature of the ventricles in a normal heart does not invert during systole, thus rendering such motions grossly abnormal. A healthy heart, moreover, will resist having its curvature inverted and heart function needs to decline by 30% before the effect of "non-uniform direct cardiac compression" becomes noticeable. In short, the heart resists assist when a DCCD induces aberrant strains. DCCD devices described above induce motions that are grossly abnormal. The Vineberg device inverts curvature in long axis planes and short axis planes. The Anstadt cup and Cardio-Support System invert curvature in long axis planes yet preserve curvature in the short axis planes. The AbioBooster, DCC Patch, Hewson device, and Parravicini devices pull on the interventricular sulci and push on the freewall such that the curvature will increase at the sulci and decrease on the freewalls. The Heart Booster inverts curvature in short axis planes, yet preserves curvature in the long axis planes. Because they were not designed to eliminate aberrant motions, it should not be surprising that these existing DCCDs described above induce aberrant strain patterns.

Additionally, none of the existing DCCDs described above are implanted in a minimally invasive fashion, and such an implantation method is highly desirable, clinically useful, and commercially advantageous. Given that strain is a primary stimulus of myocardial growth and remodeling, there is a need for a DCCD that eliminates dyskinetic or hypokinetic motions in the heart.

This device, described in U.S. patent application Ser. No. 10/870,619, filed Jun. 17, 2004 (the '619 application), which is incorporated by reference herein, is the first implantable device to proactively modulate the strain pattern during contraction. The class of devices claimed in the '619 application are those that apply direct cardiac compression in a manner such that the end-diastolic and end-systolic configurations are physiologic with normal cardiac curvature, i.e. the class of direct cardiac compression device that achieve cardiac rekinesis therapy. The device disclosed in the '619 application must be attached to the valve plane of the heart. An attachment developed in benchtop trials consists of suture runs along the right and left free walls together with stents that go from the device shell to the center of the valve plane via the transverse pericardial sinus (anterior stent) and oblique pericardial sinus (posterior stent). In addition to keeping the heart in the device, the stents eliminate the need to suture near the coronary arteries in the interventricular sulci. The highly elastic membrane on the epicardial surface is sealed tightly with the rigid shell to contain the pneumatic driving fluid (e.g., air). A typical membrane requires about 1 kPa (10 cm H20) of vacuum to unimpede heart filling. This is similar to that of the native heart which typically requires about 9 cm H20 of transmural pressure to fill (e.g., 6 cmH20 of venous pressure minus a negative 3 cm H20 of intrathoracic pressure). The pressure waveforms (with compression for systole and tension for diastole) were generated by a Superpump System made by Vivitro Systems Inc. for cardiovascular research. The sync out signal was amplified, made bipolar, and used to pace the heart via right atriam (RA) leads.

One method of overcoming some negative effects of a hard-shelled DCCD (e.g., the need for a large thoracotomy) is to use a soft-shelled device. Soft-shelled devices include DCCDs with primary components that are constructed out of highly deformable materials. Such DCCDs can be collapsed and possibly implanted through a small incision this is likely to be sub-xiphoid (e.g., inferior to the xiphoid process) or a left thoracotomy. The Abiobooster and Heart Booster are currently existing soft-shelled devices. However, as described above, both of these devices induce an aberrant strain pattern in the heart. Additionally, implantation methods for these devices still require sewing the devices to the heart or pericardium.

The above mentioned direct cardiac compression devices are active devices or assist devices that have a power source and method of delivering the power to increase cardiac output. Other devices that contact the outer surface of the heart are cardiac support devices and diastolic recoil devices. Cardiac support devices are useful for limiting the heart size, but they constrict the heart and thus impede filling (at best, they do not impede filling until some limit point where size of the heart is limited). Dynamically adjustable support devices are further useful because the limit point can be controlled to additionally decrease the size of an enlarged heart. Diastolic recoil devices are useful for increasing the recoil or filling of the heart, but they do not necessarily limit the heart size.

What is desired is a mechanical oriented device and therapy designed to optimize the mechanical environment for heart growth and remodeling that are restorative and potentially rehabilitative in nature.

SUMMARY OF THE INVENTION

The present invention is a mechanical oriented therapy designed to optimize the mechanical environment for heart growth and remodeling that are restorative and potentially rehabilitative in nature. More specifically, the present invention is an extra-cardiac, biphasic and dynamic support and diastolic recoil device with intrinsic pneumatic attachment to the exterior surface of the heart, with a mechanism to enable heart motions such as twisting and contracting, and/or a combination of the recoil device with adjustable passive support and/or active assist so to treat both systolic and diastolic causes of heart failure. The device action of the present invention is biphasic with a "filling impediment" phase and with a "filling enhancement" phase. The "filling impediment" phase reduces heart size and alleviates the problems associated with cardiac dilatation. The "filling enhancement" phase assists the heart fill during diastole and alleviates the problems associated with diastolic dysfunction. The present invention further comprises a diastolic recoil mechanism device that is biphasic about a "limit point" with "filling enhancement" for cardiac volumes below the limit point and "filling impediment" for cardiac volumes above the limit point. In a further embodiment, the limit point of the present invention can be dynamically adjustable post implantation.

The present invention is a mechanical oriented therapy designed to optimize the mechanical environment for heart growth and remodeling that are restorative and potentially rehabilitative in nature. The present invention is a recoil device with intrinsic pneumatic attachment to the exterior surface of the heart, with a mechanism to enable heart twisting motion, and/or a combination of the recoil device with adjustable passive support and/or active assist so to treat both systolic and diastolic causes of heart failure. Some embodiments of the present invention produce a normal cardiac strain pattern while other embodiments eliminate or reduce abnormal strain patterns. By eliminating aberrant strain patterns with the present invention, abnormal growth and remodeling is retarded and becomes restorative. Further, by eliminating hypokinesis, for example, the device may reduce apoptosis, enhance myocyte development from native stem cells, and lead to ventricular recovery.

The present invention provides a direct cardiac contact device adapted to be implanted in a patient suffering from congestive heart failure and related cardiac pathologies, said cardiac device having means for providing ventricular assist, ventricular support and diastolic recoil, or for providing ventricular support and diastolic recoil only.

The device includes a means for determining a phase transition point (target end diastolic volume (TEDV)) that may be adjustable or provide a means for dynamic adjustable support in some embodiments. For cardiac volumes below TEDV, the device enhances filling in a filling enhancement phase and for cardiac volumes above TEDV the device impedes filling in a filling impediment phase.

The device provides an adjustable passive support component that continually applies support to the epicardial surface of the heart, thereby promoting reverse remodeling. In addition the method may include the step of adjusting the support wherein, as the diseased heart begins to respond to the support by becoming smaller, the TEDV can be adjusted to provide the same amount of support as the initial treatment intervention.

The present invention may also include a diastolic recoil enhancement having elastic memory component which is utilized when cardiac pressures are lower than TEDV by creating a negative pressure that promotes ventricle filling and when cardiac pressure exceeds TEDV, the device acts to constrain filling and cardiac volume. The diastolic recoil device is adapted to remain deployed about the heart via intrinsic pneumatic attachment without suturing or any direct attachment method.

The device may include one or more elastic energy storing elements that is a frame or mesh made of shape memory alloys or polymers. The device may also include components designed to provide adjustable passive support, active assist, or a combination of active assist and adjustable passive support to a damaged or diseased heart. The diastolic recoil device also includes imparting a twisting motion to a heart as it is contracted and then untwists as it recoils. The present invention also includes a diastolic recoil device for assisting a diseased or damaged heart by providing direct cardiac contact that compresses the heart during contraction without inverting or significantly perturbing the curvatures of the heart.

The present invention includes a method of using a direct cardiac contact ventricular assist, ventricular support and diastolic recoil by determining a phase transitioning point (target end diastolic volume (TEDV)); and operating in a biphasic mode about an adjustable phase transition point (TEDV). The method may also include enhancing filling in a filling enhancement phase when cardiac volumes are below TEDV and or and impeding filling (i.e., "filling impediment" phase) when cardiac volumes above TEDV.

The present invention includes a direct cardiac contact diastolic recoil device to improve diastolic recoil of a heart and reduce postoperative pericardial adhesion. The device includes a first biocompatible film for adhesion to the epicardial surface of the heart; a second biocompatible film for adhesion to the chest cavity, one or more fluid filled bladders that separate the first biocompatible film and the second biocompatible film to prevent adhesion between the epicardial surface of the heart and the chest wall; and one or more structural elements in contact with the first biocompatible film, the second biocompatible film or both to store elastic energy during heart contraction and release energy during heart filling.

BRIEF DESCRIPTION OF THE DRAWINGS

A more complete understanding of the present invention may be obtained by reference to the following Detailed Description, when taken in conjunction with the accompanying Drawings, wherein:

FIGS. 2A-2B are schematic diagrams of the cross-section, top down view, of a device according to one embodiment of the present invention without a heart inside, wherein FIG. 2A is in the deflated state and FIG. 2B is in the pressurized state;

FIGS. 3A-3B are schematic diagrams of the long-section of a device according to one embodiment of the present invention without a heart inside, wherein FIG. 3A is in the deflated state and FIG. 3B is in the pressurized state;

FIGS. 4A-4B are schematic diagrams of the cross-section of a device according to one embodiment of the present invention with a heart inside, wherein FIG. 4A is in the deflated state and FIG. 4B is in the pressurized state;

FIGS. 5A-5B are schematic diagrams of the long-section of a device according to an embodiment of the present invention with a heart inside, wherein FIG. 5A is in the deflated state and FIG. 5B is in the pressurized state;

DETAILED DESCRIPTION OF THE INVENTION

Figure 1A:
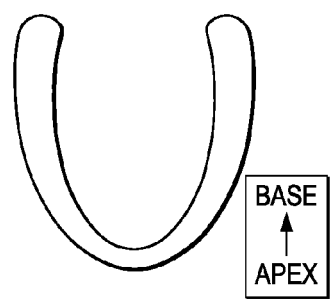
FIGS. 1A-1D are diagrams showing the normal, null and inverted curvature in apex-to-base, radial plane of the heart.
Figure 1B:
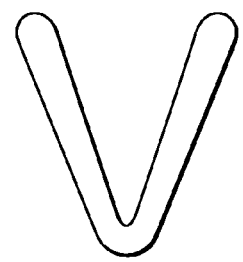
Figure 1C:
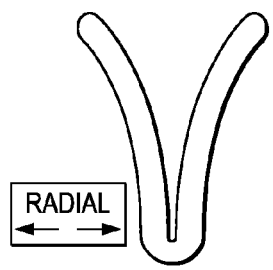
Figure 1D:
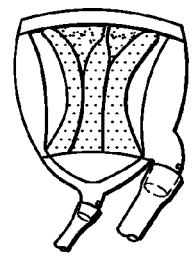

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the "cardiac rekinesis therapy" is the restoration of physiological or beneficial motion to the heart, or in other words, to eliminate aberrant or pathophysiological motions or strains, as opposed to circulatory assist therapies.

As used herein, a "biomedical material" is a material which is physiologically inert to avoid rejection or other negative inflammatory response.

The present invention will now be described more fully with reference to the accompanying drawings, in which preferred embodiments of the present invention are shown. The present invention may, however, be embodied in many different forms and should not be constructed as limited to the embodiments set forth herein; rather, these embodiments are provided so that this disclosure will be thorough and complete, and will fully convey the scope of the present invention to those skilled in the art.

The present invention comprises a contoured diastolic recoil device that enhances diastolic recoil of a damaged or diseased heart. The diastolic recoil device does not need to be sutured or directly attached to the heart. Rather, the diastolic recoil device intrinsically attaches to the heart via pneumatic locking. In operation, there is no free air in the chest between the device and heart so if the heart becomes smaller (due to ejection of blood), the device is pulled inward. Likewise, when the device pushes outward, it applies a suction-like traction to the heart. If free air were present in the chest, which it normally is not, the suction-like traction would draw air between the device and heart. However, with no free air, the suction traction is applied directly to the heart surface. This pneumatic locking, or intrinsic pneumatic attachment, is illustrated by analogy: it is very difficult to pull a water balloon out of a cup when they are placed inside of a bag in which the air has been evacuated (i.e., like a closed chest). After air in the mediastinum is removed, the heart and device are pneumatically locked in a co-axial configuration.

The diastolic recoil device of the present invention uses the intrinsic pneumatic attachment and its elastic properties to enhance the diastolic recoil of the heart. At the end of systole and the beginning of diastole the diastolic recoil device of the present invention acts like a loaded spring, applying negative pressure to the exterior epicardial surface of the heart, helping the ventricles of the heart to fill.

The present invention is a significant innovation in the cardiac device industry, as it can address both systolic and diastolic heart failure with a single device design. The present invention can be used with patients having either systolic or diastolic heart failure but also those with combined systolic and diastolic failure. Conventional passive devices for treating systolic heart failure are designed to provide mechanical constraint and support of an enlarged myocardium; but, unlike the present invention are not adjustable following implant. Further, such conventional devices lack the ability to sustain reduction of the left ventricular dimensions. Moreover, the conventional devices are designed to fibrose to the heart surface to stabilize the device-heart interaction. The present invention can be adjusted post implant. The ability to adjust the device of the present invention following implant provides a proactive means to constrain and gradually reduce hypertrophy in the diseased heart. Accordingly, the present invention, with its diastolic recoil design, also addresses the problem of diastolic heart failure. The present invention provides a means for stimulating cardiac remodeling events under conditions that are restorative toward full cardiac rehabilitation.

The present invention comprises a minimally-invasive device that is deployed into the pericardial space surrounding the heart for modulating the mechanics of a failing heart. The adjustable passive support and diastolic recoil technology achieves ventricular size reduction and also enhanced ventricular filling in both systolic and diastolic heart failure patients.

Though different devices exist today with specific indications for medium/long term support, the minimally invasive implantable device of the present invention is the first device which provides an adjustable passive support and diastolic recoil technology integrated in a same device design.

The adjustability of the device enables cardiologists to proactively intervene in heart failure whereby specific mechanical conditions can be generated and employed to direct growth and remodeling events that are restorative and/or rehabilitative in nature. In particular, the present invention can directly shift the end-diastolic pressure volume relationship (EDPVR) to the left, i.e., toward lower volumes and reduced LV size.

The present invention minimizes invasiveness, infection, and coagulation. Heart replacement is highly invasive and induces great trauma on the patient and complications from anti-rejection medication. Current, blood-contacting assist technologies are greater risk for blood trauma, clotting activation, and sepsis. Blood-contacting assist technologies cannot be started and stopped because of clot formation. The present invention can be used in combination therapies which combine mechanical, electrical, pharmaceutical, and/or stem cell therapies.

The present invention enables an integrated research approach for correcting both systolic and diastolic heart failure in patients with either one of the ventricular dysfunctions or combined systolic and diastolic dysfunction.

The present invention comprises a contoured diastolic recoil device that reduces dyskinesis and hypokinesis. The device of the present invention includes a selectively inflatable end-systolic heart shaped bladder with one or more contoured supports configured to surround at least a portion of the heart to provide curvatures similar to the proper shape of the heart when pressurized and one or more fluid connections in communication with the selectively inflatable end-systolic heart shape bladder for pressurization and depressurization.

The one or more contoured supports form one or more inflatable compartments having an expanded curvature are optimized to fit generally the proper end-systolic shape of the heart. The selectively inflatable end-systolic heart shaped bladder comprises an inner membrane that is at least partially folded when depressurized and at least partially unfolds when pressurized.

The one or more contoured supports may include one or more dividers individually of similar or different materials, one or more wires individually of similar or different materials or a combination thereof to form a shape generally appropriate to the proper end-systolic shape of the heart. The selectively inflatable end-systolic heart shaped bladder includes a material that is substantially biocompatible, fluid-impermeable and substantially elastic. For example, at least a portion of the device may be made from elastomeric polyurethane, latex, polyetherurethane, polycarbonateurethane, silicone, polysiloxaneurethane, hydrogenated polystyrene-butadiene copolymer, ethylene-propylene and dicyclopentadiene terpolymer, hydrogenated poly(styrene-butadiene) copolymer, poly(tetramethylene-etherglycol) urethanes, poly(hexamethylenecarbonate-ethylenecarbonate glycol) urethanes and combinations thereof.

The selectively inflatable end-systolic heart shaped bladder is generally collapsible when depressurized and is reinforced to resist radially outward expansion during pressurization. The device of the present invention may take many configurations depending on the particular treatment. For example, the selectively inflatable end-systolic heart shaped bladder may include 12 inflatable tapered compartments formed by the one or more contoured supports to provide an expanded curvature similar to the proper end-systolic shape of the heart; however, other embodiments may have 1 or more inflatable tapered compartments. Furthermore, the distribution of the inflatable tapered compartments may vary from the design of 4 chambers on the RV side and 8 chambers that are mostly on the LV but also overlapping the interventricular sulci. For example, the device may have 1 to 12 or more chambers on the RV side and 1 to 24 or more chambers that are mostly on the LV and overlapping the interventricular sulci.

The inflatable tapered compartments are connected to a fluid pressure source through an inlet port and an outlet port. The device is inflated with a positive pressure during systole and deflated via suction during diastole. Other configurations and multiple connections are also possible depending on the particular application and configuration.

The present invention further comprises a contoured diastolic recoil device that applies forces to the exterior, epicardial boundary of the heart to restrict inflow and modulate right flow versus left flow through the heart. The device includes a selectively inflatable end-diastolic contoured bladder having one or more contoured supports configured to releasably engage the heart. The one or more contoured supports protrude inward towards the right ventricle to decrease the end-diastolic volume of the right ventricle during diastole. The device also has an inlet connection and outlet connection in communication with the selectively inflatable end-diastolic contoured bladder to pressurize and depressurize the selectively inflatable end-diastolic contoured bladder. Residual pressure is applied about the right ventricle to not fully deflate during diastole. Generally, the inlet line is in communication with the inlet connection to operatively expand the selectively inflatable end-diastolic contoured bladder and an outlet line is in communication with the outlet connection to operatively withdraw fluid from the selectively inflatable end-diastolic contoured bladder. This allows connection to conventional devices to apply and remove pressure or custom devices specifically for the present invention.

Once access to the heart of the patient is provided, the present invention, being a selectively inflatable end-systolic heart shaped bladder can be positioned about at least a portion of the periphery of the heart. The selectively inflatable end-systolic heart shaped bladder is then connected to a fluid source to inflate the selectively inflatable end-systolic heart shaped bladder with a positive pressure during systole and deflate the selectively inflatable end-systolic heart shaped bladder during diastole. Alternatively, the selectively inflatable end-systolic heart shaped bladder is connected to the fluid source before positioning and subsequently activating to inflate and deflate the selectively inflatable end-systolic heart shaped bladder.

The present invention further comprises a contoured diastolic recoil device that reduces dyskinesis and hypokinesis having an end-systolic heart contoured bladder with one or more contoured supports configured to surround at least a portion of the heart to provide curvatures that are similar to the proper end-systolic shape of the heart.

The present invention further comprises a method for promoting a physiological mechanical environment conducive to cardiac stem cell proliferation and differentiation into functional cardiomyocytes. The method includes providing access to a heart of a patient and positioning a selectively inflatable end-diastolic heart shape bladder about at least a portion of the periphery of the heart. The selectively inflatable end-diastolic heart shape bladder is connected to a fluid source to the selectively inflatable end-diastolic heart shape bladder to inflate with a positive pressure during systole and deflate the selectively inflatable bladder during diastole. The residual pressure is applied about the right ventricle to not fully deflate during diastole.

The present invention further comprises a selectively inflatable end-diastolic heart shape bladder that includes a pressurizable chamber formed by an inner membrane and an outer membrane and one or more contoured supports positioned within the pressurizable chamber to provide curvatures that are similar to the proper end-diastolic shape of the heart when the pressurizable chamber is pressurized. The one or more end-diastolic contoured supports form one or more inflatable compartments having an expanded curvature optimized to fit the heart geometry similar to the proper end-diastolic shape of the heart.

The diastolic recoil device that applies forces to the exterior, epicardial boundary of the heart optimized to fit an end-systolic shaped heart geometry is provided by the present invention. The diastolic recoil device includes a selectively inflatable bladder having one or more end-systolic contoured supports configured to surround at least a portion of the periphery of the heart and provide curvatures similar to the proper end-systolic shape of the heart when the pressurizable chamber is pressurized and one or more fluid connections in communication with the selectively inflatable bladder to pressurize and depressurize the selectively inflatable bladder.

The present invention further comprises a diastolic recoil device that may separately modulate the end-systolic and end-diastolic configurations of the heart. Of the selectively inflatable compartments or bladders, some may be specifically designed to only inflate during systole while others are designed to remain inflated during systole and diastole. By inflating during diastole, the diastolic recoil device can regulate the end-diastolic volume and shape of the heart and by selectively inflating during systole the diastolic recoil device can regulate the end-systolic volume and shape of the heart.

The present invention further comprises a diastolic recoil device that promotes a contraction strain pattern on a diseased or damaged heart that reduces dyskinetic or hypokinetic motions. The device includes a selectively inflatable end-systolic heart shaped bladder with one or more contoured supports configured to surround at least a portion of the heart to provide curvatures that are similar to the proper shape of the heart when pressurized. The device also includes one or more fluid connections in communication with the selectively inflatable end-systolic heart shaped bladder for pressurization and depressurization.

The present invention further comprises a method of assisting a diseased or damaged heart including providing a diastolic recoil device that compresses the heart during contraction without inverting or significantly perturbing the curvatures of the heart by positioning a selectively inflatable end-systolic heart shape bladder about at least a portion of periphery of the heart once access is made to the heart of the patient. The next step is the activating of a fluid source to the selectively inflatable end-systolic heart shape bladder to inflate with a positive pressure during systole and deflate the selectively inflatable bladder during diastole.

The present invention further comprises a diastolic recoil device that applies forces to the exterior, epicardial boundary of the heart optimized to fit an end-systolic shaped heart geometry. The device includes two or more contoured compartments, an inlet connection and an outlet connection. The two or more contoured compartments are configured to surround at least a portion of the heart and are individually contoured to provide curvatures that are similar to the proper end-systolic shape of the heart when pressurized. The inlet connection is in communication with the two or more inflatable contoured compartments and an outlet connection in communication with the two or more inflatable contoured compartments.

The present invention further comprises a dyskinesis and hypokinesis reduction system including a contoured heart assist device and a pressurization apparatus. The contoured heart assist device includes a selectively inflatable end-systolic heart shaped bladder with one or more contoured supports configured to surround at least a portion of the heart to provide curvatures similar to the proper shape of the heart when pressurized and one or more fluid connections in communication with the selectively inflatable end-systolic heart shape bladder for pressurization and depressurization. The pressurization apparatus in communication with the one or more fluid connections of the contoured heart assist device includes a pressurization mechanism and a depressurization mechanism. The pressurization apparatus can apply pressure to the contoured heart assist device and remove pressure from the contoured heart assist device. The pressurization apparatus is controllable to allow for different cycling rates between pressurized and depressurized states.

The present invention further comprises a diastolic recoil device, particularly a soft-shelled direct cardiac compression device, and methods of implanting it. In particular it is directed to a soft-shelled direct cardiac compression device that proactively modulates the strain pattern in the heart during contraction so as to reduce apoptosis in the myocardium and/or induce a beneficial growth and remodeling of the myocardium and/or a beneficial mechanical environment conducive to cardiac stem cell regeneration. In particular, the device of the present invention does not invert or grossly perturb the curvature of the heart during contraction.

In certain embodiments of the present invention, the strain pattern is a physiological strain pattern, near physiologic strain pattern or a strain pattern that is not aberrant. A physiological strain pattern, for the purposes of the present invention, is one which does not invert or grossly alter the heart's curvature during systole. The present invention also maintains a normal curvature or strain pattern during diastole, or relaxation of the heart.

Certain embodiments of the present invention, when implanted in a patient, for example to eliminate dyskinesis in the borderzone, preserves myocardium and minimizes infarct expansion and promotes cardiac stem cell proliferation and differentiation into functional cardiomyocytes.

In most cases, the device of the present invention may be inserted through a small incision. Devices of the present invention may also be attached to the atrial appendages via clamps that may also be used to synchronize the device to the electrocardiogram (ECG) or to pace the heart relative to the device activation.

Certain embodiments of the present invention can be used in conjunction with cardiac stem cell therapies. Stem cells used for cardiac regeneration therapy include but are not limited to stem cells derived from embryonic stem cells, somatic stem cells taken from bone marrow, progenitor cells from cardiac tissue, autologous skeletal myoblasts from muscle tissue, hematopoietic stem cells, mesenchymal stem cells, and endothelial precursor cells. The present invention can also be used in combination naturally occurring cardiac stem cells. Transplanted stem cells may be injected directly into cardiac tissue including, infarcted regions, cardiac scar tissue, borderzones, or healthy cardiac tissue. Transplanted stem cells may also be injected systemically feeding regions of cardiac tissue and may migrate to regions of the damaged or diseased heart and engraft to regions of the damaged or diseased heart. Transplanted stem cells may also provide diffusible products to regions of the damaged or diseased heart.

In operation, the present invention applies forces to the exterior, epicardial surface of the heart to promote a physiological mechanical environment in order to mechanically stimulate stem cells to differentiate into functional cardiomyocytes and engraft to a diseased heart. The following description is of various embodiments of a diastolic recoil device designed to apply such forces.

The present invention comprises a diastolic recoil device that applies forces to the exterior, epicardial boundary of the heart such that transplanted stem cells are subjected to strain patterns typically associated with normal cardiac mechanics. The diastolic recoil device can manipulate the mechanical environment about the heart such that stem cells are stimulated to grow, repopulate and differentiate into functional cardiomyocytes via mechanical factors. The diastolic recoil device can promote a contraction strain pattern on a diseased or damaged heart that reduces dyskinetic and/or hypokinetic motions by providing direct cardiac compression to a diseased or damaged heart that compresses the heart during contraction without inverting or significantly perturbing the curvatures of the heart.

To model the treatment paradigm for embodiments of the present invention and grossly estimate what driving pressures are needed, one may use Laplace's law for a spherical vessel which gives an average wall stress ("$\sigma$") based on average radius ("R"), thickness ("H") and transmural pressure difference ($P_{in}-P_{out}$) where $P_{in}$ is the pressure in the ventricle and $P_{out}$ is the pressure outside the ventricle. In particular, $\sigma=(P_{in}-P_{out})H/2R$ Because blood is nearly incompressible, flow is dominated by pressure gradients (or less accurately by pressure differences). Without loss in generality, one may define blood pressure as its difference from atmospheric pressure. Because of rarification and densification, flows in compressible fluids are mediated by both pressure gradients and absolute pressure. Often $P_{out}$ is judiciously chosen as zero, yet for the present calculations, it is an important parameter because selected devices of the present invention are modulating $P_{out}$ by applying pressure to the epicardial surface of the heart. The focus of certain embodiments of the present invention thus is to increase $P_{out}$ to obtain a lower $\sigma$ and thus greater motion or ejection. For a large, thin, and hypokinetic heart, one may need to make $\sigma$ at least as low as a normal heart.

Let $P_{in}$ be a typical mean systolic pressure (e.g., 7.5 kPa or approximately 100 mmHg). A typical thickness-to-radius ratio at end-diastole for a normal adult sheep is 1 to 2.5; whereas for overloaded, remodeled myocardium (as in the apical aneurysm model of Guccione et al., 2001) the thickness-to-radius ratio is about 1 to 4.

Using the equation above, to normalize $\sigma$ with the same $P_{in}$, a $P_{out}$ of 2.8 kPa is needed. This is similar to the maximum driving pressure (approximately 3 kPa) used in in vitro tests described further in Example 2. For ventricular recovery, external pressures are likely needed that are about the same order as or slightly higher than pulmonary artery pressure. Hence, right ventricle ("RV") ejection fraction is expected to be nearly 100%. External pressure is transferred through the incompressible RV myocardium and incompressible blood in the RV chamber, while RV outflow is accelerated. It has been demonstrated that uniform pressure applied to the entire epicardial surface will assist the heart at all levels of contractility.

Certain embodiments of the present invention can decrease RV input to compensate for the expected increase in RV output. Absent this capability, it is likely that the RV and healthy regions of the LV would atrophy due to excessive off-loading. However, certain embodiments of the present invention are ideal for weaning or gradually decreasing Pout, and the use of clenbuterol which has been shown to be useful in achieving ventricular recovery by preventing atrophy.

One embodiment of the present invention is a soft-shelled DCCD that has inflatable, longitudinally oriented chambers that when deflated are collapsible, allowing for minimally invasive implantation. In addition, the deflated chambers are shaped and adjoined to form a structure that allows typical diastolic configurations. When pressurized the chambers push on the exterior of the heart in such a way as to induce a systolic configuration with normal curvatures.

Figure 2A:
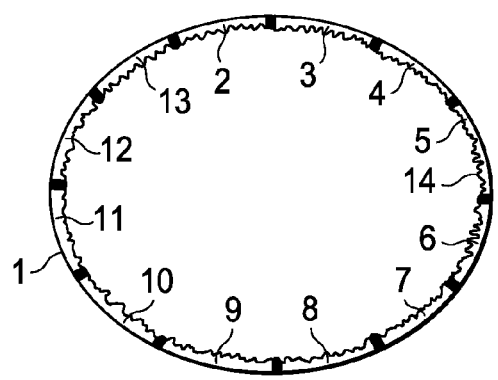
Figure 2B:
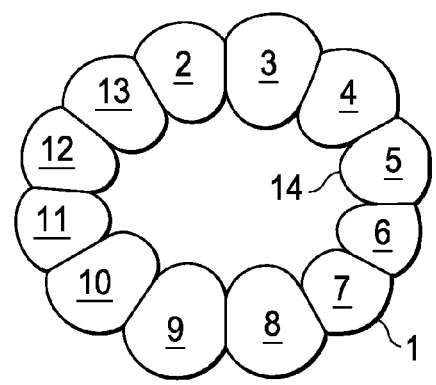

FIGS. 2A and 2B illustrate a horizontal cross section of one embodiment of the device 1 of the present invention in the deflated state, as seen in FIG. 2A and the inflated state in FIG. 2B. The device 1 includes 12 chambers 2-13 arranged with 4 chambers on the RV side and 8 chambers that are mostly on the LV but also overlapping the interventricular sulci. The chambers 2-13 are constructed from polyethylene film in one embodiment; however, other materials may be used. The side of the chambers 2-13, that are on the outer boundary, form a shape that is similar to the end diastolic shape of the heart. The interior surface 14 has folds and crenulations such that when inflated the chambers 2-13 mostly expand inward.

Figures 3A, 3B:
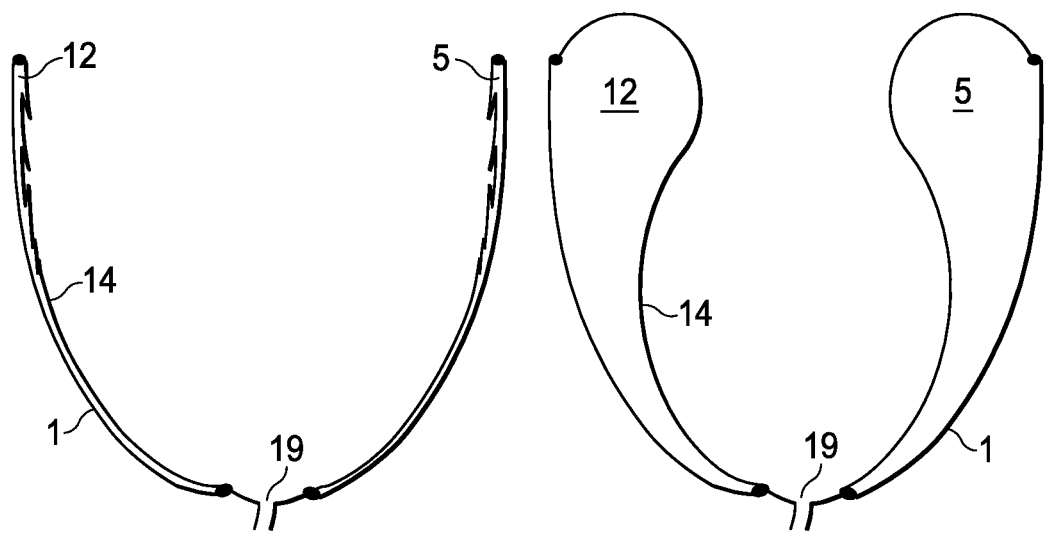

FIGS. 3A and 3B illustrate a vertical cross section of one embodiment of the device 1 of the present invention in the deflated state as seen in FIG. 3A and the inflated state in FIG. 3B. Device 1 includes chambers 5 and 12 in the inflated and deflated states using access port 19. The interior surface 14 of the chambers 2-13 that are on the outer boundary form a shape that is similar to the end diastolic shape of the heart. The interior surface 14 has folds and crenulations such that when inflated the chambers 2-13 mostly expand inward to contact the epicardium 16 of the heart 15.

Figures 4A, 4B:
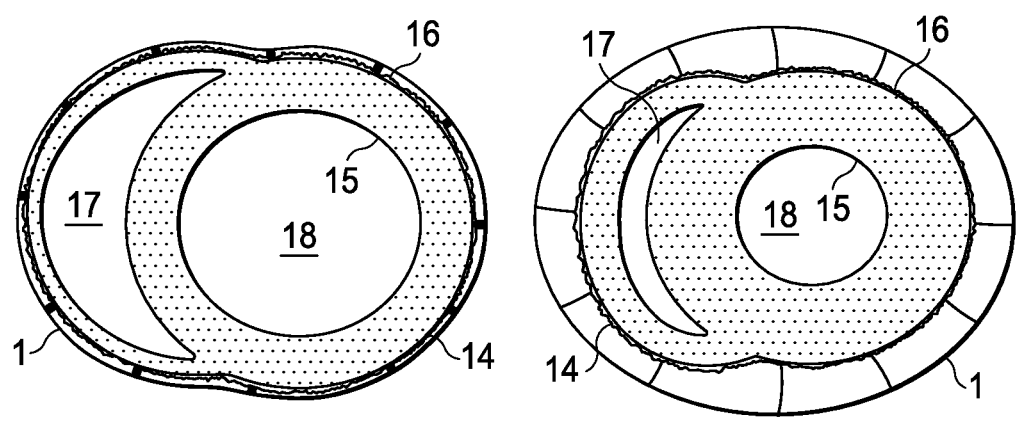

FIGS. 4A and 4B illustrate a horizontal cross section of one embodiment of the device 1 of the present invention fitted to the heart 15. FIG. 4A is in the deflated state and FIG. 4B is in the inflated state. The device 1 includes 12 chambers 2-13 arranged with 4 chambers on the RV side and 8 chambers that are mostly on the LV but also overlapping the interventricular sulci. The chambers 2-13 include interior surface 14 that contacts the epicardium 16 of the heart 15. The side of the chambers 2-13 that are on the outer boundary form a shape that is similar to the end diastolic shape of the heart. The interior surface 14 has folds and crenulations such that when inflated the chambers 2-13 mostly expand inward. The shape of the interior regions of the heart 17 and 18 can be compared in the inflated state as seen in FIG. 4B and the deflated state in FIG. 4A.

Figures 5A, 5B:
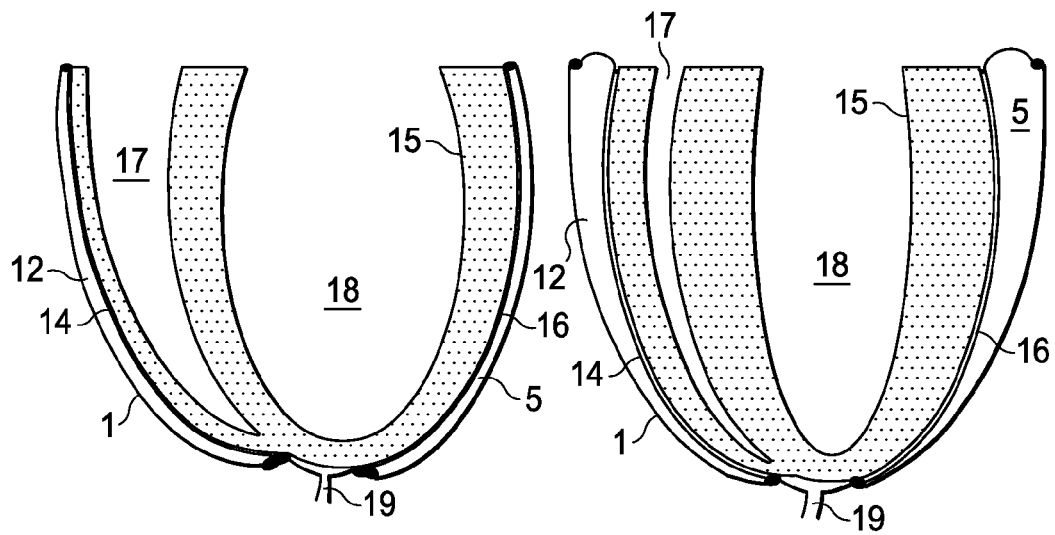

FIGS. 5A and 5B illustrate a vertical cross section of one embodiment of the device 1 fitted to the heart 15 in the deflated state as seen in FIG. 5A and the inflated state as seen in FIG. 5B. Device 1 includes chambers 5 and 12 in the inflated and deflated states using access port 19. The interior surface 14 of the chambers 2-13 that are on the outer boundary form a shape that is similar to the end diastolic shape of the heart. The interior surface 14 has folds and crenulations such that when inflated the chambers 2-13 mostly expand inward to contact the epicardium 16 of the heart 15. The shape of the interior regions 17 and 18 can be compared in the inflated state as seen in FIG. 5B and the deflated state as seen in FIG. 5A.

The fully pressurized shape without the heart inside is helpful for illustrating one embodiment of the present invention, yet the shape will be significantly different when the device surrounds a heart which contains blood under pressure as seen in FIGS. 2B and 4B. With a heart inside, the pressure in the lumen of the device is higher than the pressure in the inflatable chambers. Because the chambers cannot fully expand, the inner film of the chambers is not taut. Rather than being supported by tension in the film, e.g., FIG. 2B, pressure on the lumen side of the longitudinal chambers is supported by contact forces on the epicardial surface, e.g., FIG. 4B. Without tension on the inner film, the attachment points are not drawn inward, e.g., FIG. 2B. Instead, the shape of the outer sides of the chambers becomes circular to support the pressure within the chambers, e.g., FIG. 4B. Note how the inner membrane is crenulated and thus not under tension. Consequently, the pressure in the device chambers applies direct pressure to the heart surface. In a similar manner, a blood pressure cuff applies direct pressure to the surface of a patient's arm.

Because the inflatable chambers taper as they go from base to apex in a manner that resembles natural cardiac curvature as seen in FIG. 3B, the apex of the heart will have a physiological curvature. Moreover, because the device is rigid when pressurized, the curved shape of the apical end will act to prevent the heart from being expelled from the device. Basically, for the heart to leave the device the apical shape would have to pucker or a vacuum would need to form in the apical end of the device, both of which are unlikely.

FIGS. 3 and 5 show the access port 19 on the apex (i.e., the hole in the bottom of the device) which is useful for implantation and for removing fluid that could accumulate between the heart and device. Additionally, a biocompatible lubricant, anti-clotting, anti-fibrosis, pharmaceuticals, or antibiotic agent may be injected into the space between the heart and device. So that the device may be removed easily after weaning, the device may be covered with a film that retards fibrous adhesions such as Surgiwrap®.

As noted above, because the RV operates at a lower pressure and has a thin wall, certain diastolic recoil devices of the present invention will enhance RV ejection more than LV ejection. As observed in the implantation of a prototype, driving pressures that are equal to or greater than pulmonary artery pressure may occur, resulting in a 100% RV ejection fraction is expected. Pulmonary congestion may result if RV output is continuously increased relative to LV output. Auto-regulatory mechanisms may mitigate this enhancement of RV ejection over LV ejection. If not, separation of RV and LV chambers in the diastolic recoil device may be useful. In particular, it may be possible to impede RV filling with residual pressurization of the 4 RV chambers during diastole. By controlling input to the RV the ratio of RV output to LV output can be modulated.

FIG. 6 illustrates how RV input (i.e., filling) can be modulated by the application of residual RV epicardial pressure (RRVEP). During diastole, the myocardium is relaxed and the heart shape is easy to perturb. This is particularly true of the RV freewall because it is very thin. Hence, residual gas in the four chambers abutting the RV freewall will likely prevent the RV from filling while leaving the LV unperturbed. It is, in essence, easier to differentially modulate filling than to modulate ejection.

Figures 6A, 6B:
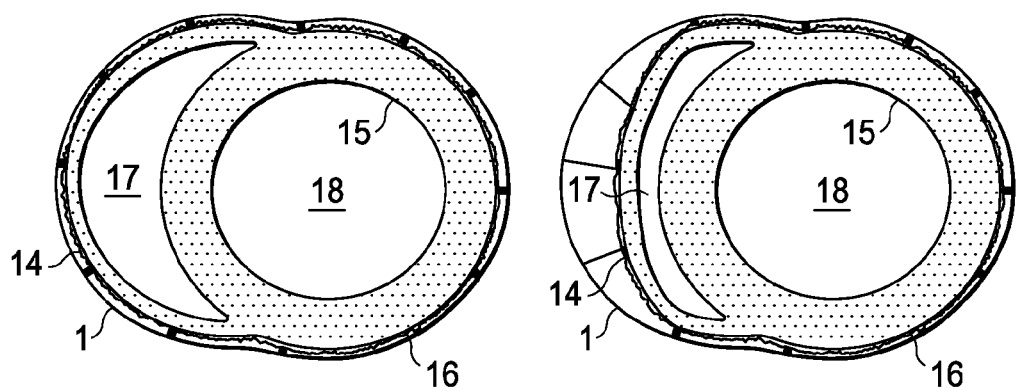
FIGS. 6A-6B are schematic diagrams of one embodiment of the present invention configured to reduce right ventricle input by reducing right ventricle filling.

FIGS. 6A and 6B illustrate a horizontal cross section of one embodiment of the device 1 of the present invention fitted to the heart 15. FIG. 6A is in the deflated state and FIG. 6B is in the inflated state. The device 1 includes 12 chambers 2-13 arranged with 4 chambers on the RV side and 8 chambers that are mostly on the LV but also overlapping the interventricular sulci. The chambers 2-13 include interior surface 14 that contacts the epicardium 16 of the heart 15. The side of the chambers 2-13 that are on the outer boundary form a shape that is similar to the end diastolic shape of the heart. The interior surface 14 has folds and crenulations such that when inflated the chambers 2-13 mostly expand inward. The shape of the interior regions 17 and 18 can be compared in the inflated state as seen in FIG. 6B and the deflated state as seen in FIG. 6A.

The present invention overcomes the disadvantage of the potential RV freewall atrophying as a result of the RV volume being chronically decreased and native RV stroke work being decreased. Advantageously, the present invention proactively modulates the strain pattern, which is ideal for weaning the heart from a device because assist can be graded. Conventional DCCDs only assist when the heart is weak enough to be grossly deformed.

At end-systole of the cardiac cycle, the present invention has a shape with curvatures that are similar to the proper end-systolic shape of the heart. The present invention is active in the sense that energy is consumed to accomplish the shape change during systole and energy is liberated to accomplish the shape change during diastole. The energy source is from a pneumatic pressure source. During systole (i.e., shape change from end-diastole to end-systole) the device is inflated with a positive pressure. During diastole (i.e., shape change from end-systole to end-diastole) the device of the present invention is deflated via suction. If enabled for RV flow restriction, the device of the present invention is not fully deflated during diastole because some residual pressure is applied to chambers that abut the right ventricle.

The present invention is soft or collapsible when deflated. In addition the present invention minimizes the risks of thrombosis and infection as there is no contact with the blood. Many of the devices in the art when pressurized or the end-systolic shape of prior devices is grossly abnormal and this is evidenced by the various schemes used to attach the DCCD to the heart (e.g., sewing to ventricle, basal drawstring, apical suction cup, etc.).

There is no need to attach the present invention to the heart because the heart is naturally drawn into the pressurized or activated device. Specifically, for the heart to leave the device (i.e., be extruded from the diastolic recoil device), the device curvature would need to invert, yet the device rigidity (when pressurized) resists curvature inversion. This is very useful because implantation time and complications due to attachment are minimized when this feature is present—i.e., when the activated shape of the device cavity (i.e., the inner wall of the diastolic recoil device which touches the epicardial or outer boundary of the heart) is nearly end-systolic shape. It can eliminate dyskinesis (defined as abnormal cardiac motions). Current evidence indicates that differentiation of cardiac stem cells into functional cardiomyocytes is influenced by mechanical stimuli such as the motion during cardiac contraction whereby the elimination of dyskinesis is of paramount importance. The device provides some of the pumping power demanded of the heart to energize or pressurize the circulatory system. Abnormal hearts often need to be "off-loaded" or be assisted with satisfying the circulatory demands of the body.

Figure 7:
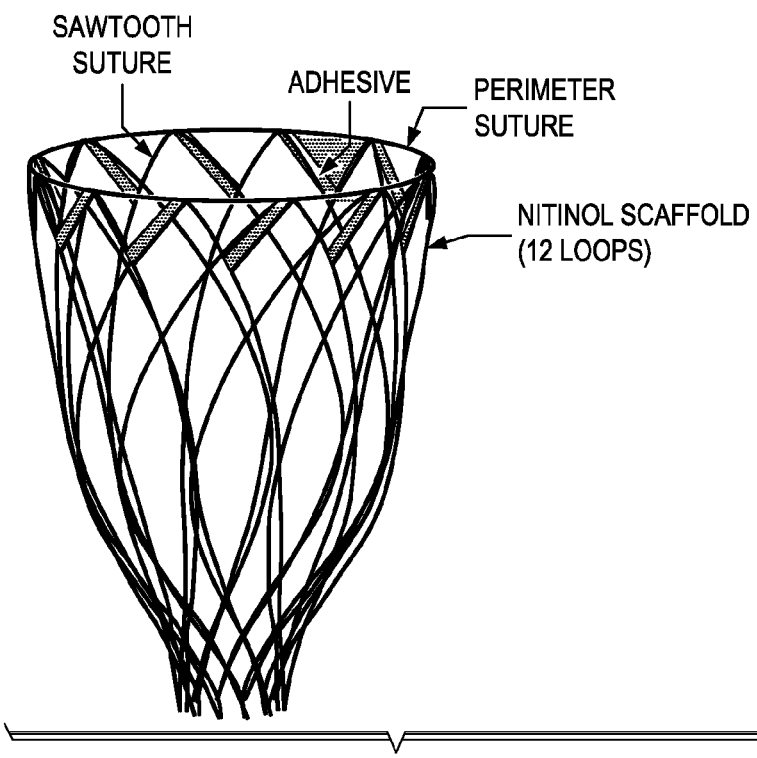
FIG. 7 is an illustration of one embodiment of the present invention wherein a nitinol scaffold is incorporated to mediate the end-diastolic configuration.
Figure 8:
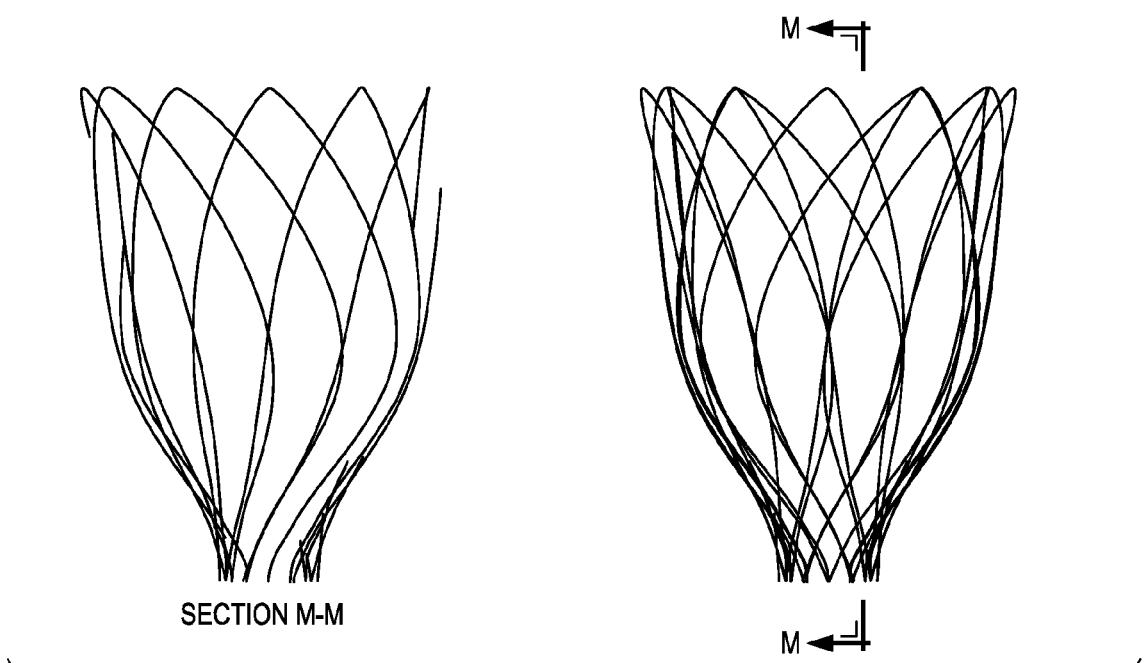
FIG. 8 is an illustration of one embodiment of the present invention wherein a nitinol scaffold is incorporated to mediate the end-diastolic configuration.

FIG. 7 is an illustration of one embodiment of the present invention wherein a nitinol scaffold is incorporated to mediate the end-diastolic configuration. FIG. 8 is an illustration of one embodiment of the present invention wherein a nitinol scaffold is incorporated to mediate the end-diastolic configuration.

Figure 9:
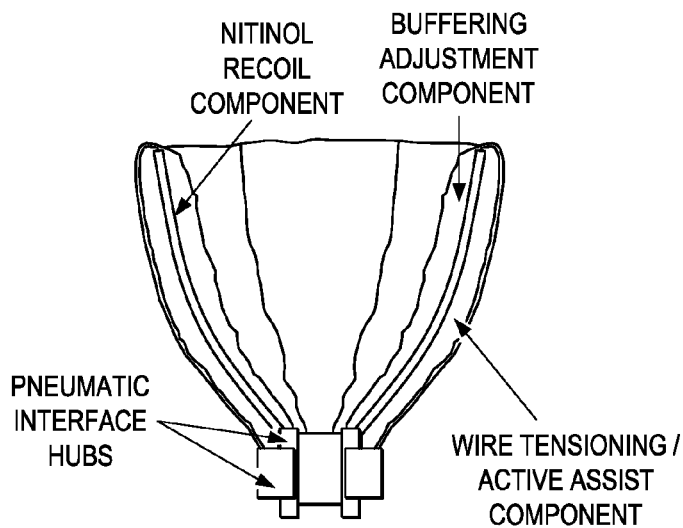
FIG. 9 is a cross-section illustration of one embodiment of the present invention depicting its support, assist, and recoil components.
Figure 10:
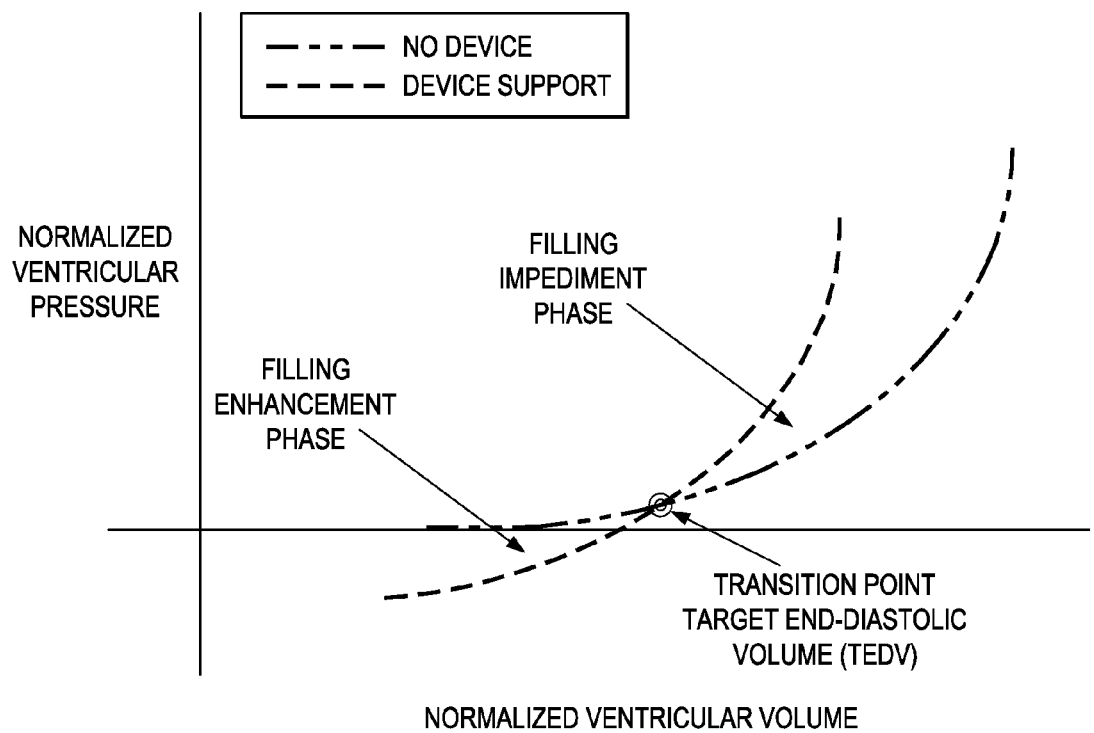
FIG. 10 is a plot which illustrates the biphasic character of the present invention.
Figure 11:
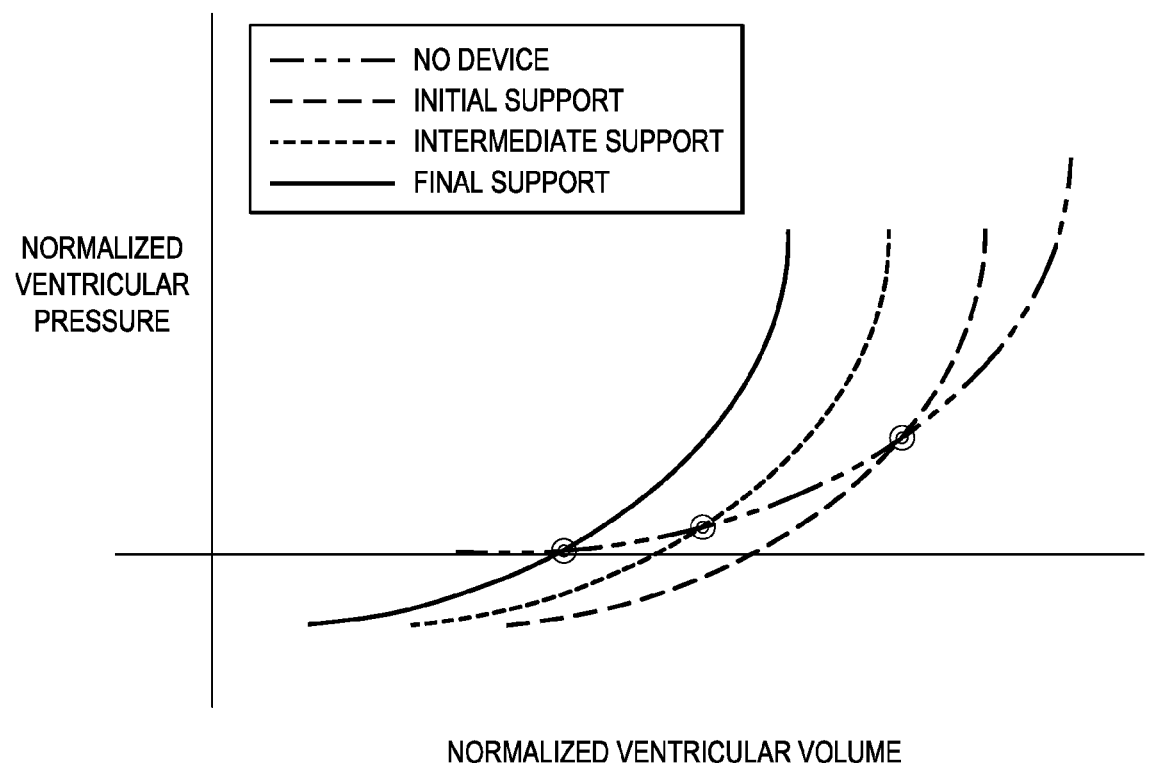
FIG. 11 is a plot which illustrates the ability of the present invention to adjust the target end-diastolic volume (TEDV) or transition point when the device of the present invention is adjusted.

The present invention comprises a biphasic and dynamic support device as illustrated in FIG. 9. The present invention is biphasic about an adjustable "phase transition point" also known as a target end-diastolic volume (TEDV). FIG. 10 is a PV plot illustrating the relationship that for cardiac volumes below TEDV, the device of the present invention enhances filling (i.e., "filling enhancement" phase), and for cardiac volumes above TEDV the device of the present invention impedes filling (i.e., "filling impediment" phase). The filling impediment of the biphasic component of the device of the present invention can be used to adjust passive support throughout the entire treatment cycle. The adjustable passive support component will continually apply support to the epicardial surface of the heart, thereby promoting reverse remodeling. As the diseased heart begins to respond to the support by becoming smaller, the TEDV can be adjusted to provide the same amount of support as the initial treatment intervention as seen in FIG. 11. The filling enhancement of the biphasic component of the present invention acts to enhance diastolic recoil. The device of the present invention has an elastic memory component that is utilized when cardiac pressures are lower than TEDV by creating a negative pressure that promotes ventricle filling. Diastolic recoil enhancement is critical for effective treatment. FIG. 10 thus demonstrates the biphasic assist component of the device of the present invention. When cardiac pressures are below the transition point, i.e., the TEDV, the device of the present invention enhances filling and increases cardiac volume, but when cardiac pressure exceed the transition point, the device of the present invention constrains filling and cardiac volume. The present invention is soft or collapsible when deflated.

Unlike conventional devices that have specific indications for support, the biphasic and dynamic support device of the present invention has a dual component of active assist and adjustable passive support. The adjustable passive support of the present invention reduces the size of an enlarged heart over a period of 6-8 months. While passive support is helpful long term, it can cause an increase in venous pressure acutely. With the dynamic support component of the present invention, this complication can be mitigated. The dynamic support component of the present invention applies active cardiac assist that restores normal cardiac motion. The dynamic support component of the present invention is configured such that when the active assist is utilized, it applies pressure to the epicardial surface of the heart, thus promoting physiological motion and increasing stroke work as needed to maintain cardiac output. The present invention can regulate the amount of dynamic assist depending on the needs of the individual and provide a means for managing cardiogenic shock.

The biphasic and dynamic support device of the present invention further comprises multiple layers of a biocompatible film with fluid filled bladders between the film layers. This structure prevents and/or reduces postoperative pericardial adhesions between the epicardial surface of the heart and the chest wall. The inner layer of the anti-pericardial adhesion device forms adhesions to the epicardial surface of the heart while the outer layer of the device forms adhesions to the chest cavity. The fluid filled bladder between the two layers acts as a barrier preventing adhesions between the epicardial surface of the heart and the chest wall. This permits easier access to the heart in case subsequent surgeries are required and also allows the heart to move freely inside the chest cavity during normal cardiac function.

The present invention provides (1) adjustable passive cardiac support and constraint by controlling the TEDV so as to facilitate the gradual reduction in size of hypertrophied diseased hearts and enhance diastolic recoil and improve pumping efficiency; and (2) active synchronous cardiac assist to maintain optimum cardiac performance, i.e., stroke volume, cardiac output, ejection fraction, stroke work, etc. and kinematics conducive to restorative remodeling processes. The present invention further creates a fluid filled barrier between the heart and chest wall to prevent pericardial adhesions and improve cardiac motion. Because the present invention does not come in contact with blood, the risks of thrombosis and infection is minimized.

Unlike conventional devices that, when pressurized, have an end-systolic shape that is grossly abnormal as evidenced by the various schemes used to attach the DCCD to the heart (e.g., sewing to ventricle, basal drawstring, apical suction cup, etc.), there is no need to attach the present invention to the heart because the heart is naturally drawn into the pressurized or activated device. Specifically, for the heart to leave the device (i.e., be extruded from the diastolic recoil device), the curvature of the device of the present invention would have to invert.

This does not occur due to the rigidity of the device that, when pressurized, resists curvature inversion. This is advantageous as implantation time and complications due to attachment are minimized when the activated shape of the device cavity (i.e., the inner wall of the diastolic recoil device which touches the epicardial or outer boundary of the heart) is in nearly end-systolic shape. Hence, this can eliminate dyskinesis, defined as abnormal cardiac motions.

Current research indicates that differentiation of cardiac stem cells into functional cardiomyocytes is influenced by mechanical stimuli such as the motion during cardiac contraction whereby the elimination of dyskinesis is of paramount importance. An advantage of the present invention is that it provides some of the pumping power demanded of the heart to energize or pressurize the circulatory system. Abnormal hearts often need to be "off-loaded" or be assisted with satisfying the circulatory demands of the body.

Another advantage of the device of the present invention is that it offers a failsafe mechanism. In particular, the device does not hinder cardiac performance when the device is deflated or deactivated. In the various embodiments described herein, the device can be completely deflated (defaulted to vacuum) to make the device soft and collapsible.

Generally when a material is implanted in the body, the body recognizes the presence of the foreign material and triggers an immune defense system to eject and destroy the foreign material. This results in edema, inflammation of the surrounding tissue and biodegradation of the implanted material. As a result, the present invention is at least partially comprised of biomedical implantable material. Examples of suitable, biocompatible, biostable, implantable materials used to fabricate the present invention include, but are not limited to, polyetherurethane, polycarbonateurethane, silicone, polysiloxaneurethane, hydrogenated polystyrene-butadiene copolymer, ethylene-propylene and dicyclopentadiene terpolymer, and/or hydrogenated poly(styrene-butadiene) copolymer, poly(tetramethylene-ether glycol) urethanes, poly(hexamethylenecarbonate-ethylenecarbonate glycol) urethanes and combinations thereof. In addition, the present invention may be reinforced with filaments made of a biocompatible, biostable, implantable polyamide, polyimide, polyester, polypropylene, and/or polyurethane.

The material used in the construction of the present invention minimizes the incidence of infection associated with medical device implantation such as entercoccus, *pseudomonas auerignosa, staphylococcus* and *staphylococcus epidermis* infections. Embodiments of the present invention include bioactive layers or coatings to prevent or reduce infections. For example, bioactive agents may be implanted, coated or disseminated on the present invention and include antimicrobials, antibiotics, antimitotics, antiproliferatives, antisecretory agents, non-steroidal anti-inflammatory drugs, immunosuppressive agents, antipolymerases, antiviral agents, antibody targeted therapy agents, prodrugs, free radical scavengers, antioxidants, biologic agents or combinations thereof. Antimicrobial agents include but are not limited to benzalkoniumchloride, chlorhexidine dihydrochloride, dodecarbonium chloride and silver sufadiazine. Generally, the amount of antimicrobial agent required depends upon the agent; however, concentrations range from 0.0001% to 5.0%.

In addition, certain embodiments of the present invention may have leads, electrodes or electrical connections incorporated into the device. When present, they may be made from noble metals (e.g., gold, platinum, rhodium and their alloys) or stainless steel. In addition, ordinary pacemaker leads and defibrillation leads can be incorporated into the present invention to provide cardiac pacing or defibrillation.

The one or more contoured supports form one or more inflatable compartments having an expanded curvature optimized to fit generally the proper end-systolic shape of the heart. The selectively inflatable end-systolic heart shaped bladder comprises an inner membrane that is at least partially folded when depressurized and at least partially unfolds when pressurized.

The selectively inflatable end-systolic heart shaped bladder is generally collapsible when depressurized and is reinforced to resist radially outward expansion during pressurization. The device of the present invention may take many configurations depending on the particular treatment. For example, the selectively inflatable end-systolic heart shaped bladder may include 12 inflatable tapered compartments formed by the one or more contoured supports to provide an expanded curvature similar to the proper end-systolic shape of the heart; however, other embodiments may have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more inflatable tapered compartments. Furthermore, the distribution of the inflatable tapered compartments may vary from the design of 4 chambers on the RV side and 8 chambers that are mostly on the LV but also overlapping the interventricular sulci. For example, the device may have 1, 2, 3, 4, 5, 6, 7, 8, 9, 10, 11, 12 or more chambers on the RV side and 1, 2, 3, 4, 5, 6, 7, 8, 9, 10, 11, 12, 13, 14, 15, 16, 17, 18, 19, 20, 21, 22, 23, 24 or more chambers that are mostly on the LV and overlapping the interventricular sulci. That chambers distribution determination for a particular application and treatment is within the scope of the skilled artisan.

The present invention also provides a direct cardiac compression device that promotes a contraction strain pattern on a diseased or damaged heart that reduces dyskinetic or hypokinetic motions. The device includes a selectively inflatable end-systolic heart shaped bladder with one or more contoured supports configured to surround at least a portion of the heart to provide curvatures that are similar to the proper shape of the heart when pressurized. The device also includes one or more fluid connections in communication with the selectively inflatable end-systolic heart shaped bladder for pressurization and depressurization.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed:

1. A method of using a direct cardiac contact ventricular assist, ventricular support and diastolic recoil device or a direct cardiac contact ventricular support and diastolic recoil device only, comprising the steps of:
    providing a biphasic direct cardiac contact device that can separately modulate an end systolic configuration and an end diastolic configuration of a heart comprising:
        an adjustable passive support component in contact with an epicardial surface of the heart to continually apply support to the heart, wherein the adjustable passive support component constrains ventricle filling when the cardiac volume exceeds a target end diastolic volume and
        an elastic memory component in contact with the adjustable passive support component wherein the elastic memory component creates a negative pressure that promotes ventricle filling when a cardiac volume is lower than a target end diastolic volume;
    determining the target end diastolic volume for the heart;
    determining a phase transitioning point from the target end diastolic volume; and
    operating the biphasic direct cardiac contact device in a biphasic mode about the phase transition point, wherein the phase transition point is an adjustable phase transition point adjustable about the target end diastolic volume for the heart.

2. The method of claim 1, further comprising the steps of:
    enhancing filling in a filling enhancement phase when cardiac volumes are below the target end diastolic volume; and
    impeding filling (i.e., "filling impediment" phase) when cardiac volumes above the target end diastolic volume.

3. The method of claim 2, wherein the filling enhancement of the biphasic component enhances diastolic recoil when the elastic memory component is utilized when cardiac pressures are lower than the target end diastolic volume by creating a negative pressure that promotes ventricle filling and when cardiac pressure exceed the target end diastolic volume, filling and cardiac volume is constrained.

4. The method of claim 1, comprising the step of using a dynamic adjustable support during the filling impediment of the biphasic component.

5. The method of claim 1, comprising the step of continually applying support to the epicardial surface of the heart, thereby promoting reverse remodeling.

6. The method of claim 1, wherein as the diseased heart begins to respond to the support by becoming smaller, adjusting the target end diastolic volume to provide the same amount of support as an initial treatment intervention.

7. A direct cardiac contact diastolic recoil device to improve diastolic recoil of a heart and reduce postoperative pericardial adhesion comprising:
    a first biocompatible film for adhesion to the epicardial surface of the heart;
    an elastic memory component in contact with the first biocompatible film wherein the elastic memory component creates a negative pressure on the heart to promote ventricle filling when a cardiac volume is lower than a target end diastolic volume;
    a second biocompatible film for adhesion to the chest cavity; and
    one or more fluid filled bladders that separate the first biocompatible film and the second biocompatible film to prevent adhesion between the epicardial surface of the heart and the chest wall.

* * * * *